United States Patent [19]

Pärtzel

[11] 4,358,945
[45] Nov. 16, 1982

[54] GAG PRESS

[75] Inventor: Karl-Heinz Pärtzel, Friedrichshafen, Fed. Rep. of Germany

[73] Assignee: Zahnradfabrik Friedrichshafen, Aktiengesellschaft, Friedrichshafen, Fed. Rep. of Germany

[21] Appl. No.: 169,471

[22] Filed: Jul. 16, 1980

[30] Foreign Application Priority Data

Jul. 17, 1979 [DE] Fed. Rep. of Germany ....... 2929731

[51] Int. Cl.[3] .................. B21D 3/10; G01H 15/00
[52] U.S. Cl. .......................................... 72/12; 72/26; 72/31; 73/584
[58] Field of Search .................. 72/389, 386, 10–12, 72/31–35, 8, 9, 26; 73/579, 584

[56] References Cited

U.S. PATENT DOCUMENTS 3,949,588 4/1976 Seo ........................................ 72/389
4,144,730 3/1979 Judge ................................. 72/389 X
4,154,073 5/1979 Galdabini ......................... 72/389 X

OTHER PUBLICATIONS

Metalloberfläche, No. 5, Published by the Hanser-Verlag in Munich, West Ger., 1979.

Primary Examiner—Francis S. Husar
Assistant Examiner—Jonathan L. Scherer
Attorney, Agent, or Firm—Karl F. Ross

[57] ABSTRACT

Piezoelectric transducers are mounted on support members of a gag press for sensing pressure vibrations arising in a workpiece in part as reflections of an initial pulse produced by the striking of the workpiece by a press ram at the initiation of a straightening operation. An electrical circuit is connected to the transducers for analyzing the sensed pressure waves and for comparing the analyzed waves to pre-established sound-threshold data stored in a memory. Upon detecting pressure waves indicative of an internal structural flaw in the workpiece, a microprocessor in the electrical circuit signals a ram drive to raise the ram and thereby terminate straightening operations, the defect-bearing workpiece being transferred to a scrap store or to a heat treatment plant by a sorter according to signals from the microprocessor. The press assembly includes position monitors juxtaposable to the workpiece in the press for determining workpiece curvature, the microprocessor being connected to these monitors and to a ram mount for adjusting in response to signals from the monitors the horizontal position of the ram prior to a downward workpiece-bending stroke thereof. Upon detecting the straightening of the workpiece according to stored tolerance data, the microprocessor elevates the ram and has the workpiece conveyed away for further finishing operations. The press assembly includes in a feeder an automatic centering or grinding apparatus and an oiling device for preparing a workpiece for sound-wave transmission over the supports to the transducers.

12 Claims, 3 Drawing Figures

GAG PRESS

FIELD OF THE INVENTION

My present invention relates to a gag press, i.e. to a press for straightening metal workpieces such as axles, billets, bars and plates upon heat treatment or tempering thereof.

BACKGROUND OF THE INVENTION

In the finishing of metal products it is common to transfer the workpieces upon heat treatment thereof to a gag press for straightening. The workpieces are subsequently examined for internal structural flaws at a testing station remote from the pressing station. In addition to the identification, localization and evaluation of internal defects, dimension measurements are implemented at the testing station for checking whether the processed workpieces conform to predetermined tolerances.

The reliability and speed of the straightening and testing operations are significant in determining the cost and the quality of construction of machinery elements.

The flaw-search techniques, such as magnetic-powder testing, X-ray examination and ultrasonic-wave monitoring, have proceeded substantially out of the experimental stage and have reached a high level of development. There are also testing techniques which yield results in the form of output signals to be used in subsequent processing operations.

A particularly effective and versatile flaw-search technique which has been recently developed comprises the analysis of pressure waves or sound waves which are emitted by a workpiece upon the striking thereof. Descriptions of the state of this art are to be found in "Metal Surfaces" ("Metalloberfläche"), No. 5, 1979, published by the Hanser-Verlag in Munich, West Germany, and in an intercompany communication from the Firm Fischer-Pierce-Walzburg of Leutkirch, West Germany, to the Zahnradfabrik Friedrichshafen, West Germany, via M. Bentley, Dunegan-Endevco (Congress 1978). The utilization of such a pressure-wave analysis technique at the testing station is, however, insufficient to enable the localization of defect causes. Because defects may be undetectably induced by the pressing apparatus itself, many workpieces sorted out at the testing station for further heat treatment and subsequent straightening will only be subjected to additional flaw-producing stressing in the press and thereby become unsuitable for the intended application. Such destruction of blanks in a refinishing process is a waste of time and energy.

Sampling the workpieces at the output of the gag press to save time results in a decrease in quality, and while it is possible to insert another testing station between the heat-treatment plant and the gag press, such an additional station would involve an increased expenditure of time and energy and a greater investment in conveyance devices and in space.

Another disadvantage of known applications of the above-mentioned pressure wave analysis technique is the difficulty of making valid comparisons of the test results of different blanks of the same production series or of the same blank before and after a second heat treatment and straightening operation, this difficulty being due at least in part to the impossibility of duplicating conditions at the testing station. Not only must each blank under comparison be supported at analogous positions and struck with the same energy at similar points, but the pressure-wave sensors of the examining apparatus must be brought to engage the blanks at similar positions on the surface thereof. Such a placement of the sensors requires highly skilled technicians.

If the testing station downstream of the press is particularly remote therefrom, the increased delay between bending and examining aggravates the difficulty of localizing sources of defects, thereby raising time and energy losses.

OBJECTS OF THE INVENTION

An object of my present invention is to provide an improved gag-press assembly including equipment for detecting internal structural flaws in the workpieces, wherein energy and time expenditure is reduced and quality control is facilitated.

Another object of my present invention is to provide such a gag-press assembly which occupies less space and has shorter transport paths and, therefore, fewer conveyance devices.

A more particular object of my present invention is to provide such a gag-press assembly in which the determination of defect causes is more easily effectuated.

SUMMARY OF THE INVENTION

A gag-press assembly for straightening a metal workpiece comprises, according to my present invention, a frame, a support on the frame at a pressing station for holding the workpiece during straightening operations, a feeder extending to the pressing station for conveying the workpiece to the support prior to the straightening operations, and a ram reciprocatably mounted on the frame at the pressing station for striking the workpiece to generate an initial sound-producing pulse and for subsequently coacting with the support to bend the workpiece. A sensor in the form of an acoustic-electric transducer is mounted on the frame for detecting pressure waves including ultrasonic waves generated by internal structural irregularities in the workpiece in response to the ram-produced initial pulse, an electrical or electronic circuit being connected to the sensor for analyzing signals therefrom to determine the presence and location and extent of internal structural irregularities in the workpiece. An adjustable mount on the frame holds the ram in a preselected one of a plurality of positions, while a drive on the frame reciprocates the ram in the mount. An extractor preferably in the form of a conveyor removes the workpiece from the passing station upon the termination of straightening operations.

According to further features of my present invention, the transducer contacts the support and is of the piezoelectric-crystal type, while an additional acoustic-electric transducer may be disposed in contact with the ram. The electrical circuit is advantageously connected to the ram drive for controlling the actuation and disengagement of the ram at least partially in response to signals from the sensor.

According to another feature of my present invention, the gag-press assembly includes two workpiece-position monitors juxtaposable to the workpiece for detecting the curvature thereof, the electrical circuit being connected to the ram mount for adjusting the position of the ram at least partially in response to signals from the position monitors.

According to yet another feature of my present invention, the electrical circuit includes a memory for storing coded sound-threshold values which are pre-established for the workpiece and a control circuit, preferably in the form of a microprocessor, connected to the memory and to the pressure-wave sensors for comparing signals therefrom with sound-threshold data from the memory, thereby determining the presence, location and extent of internal structural irregularities.

The disposition of the sound-wave sensors at the pressing station and the simultaneous execution of pressing and testing operations permits a continuous monitoring of pressure waves internally generated by a workpiece during straightening operations, thereby enabling the early detection of structural defects which might develop into fatal flaws, i.e. flaws rendering the workpiece unsuitable for subsequent utilization, but which may possibly be corrected by further heat treatment. Upon detecting such an incipient fatal flaw, the microprocessor emits to the ram drive a signal causing the same to elevate the ram and thereby terminate straightening operations.

Pursuant to further features of my present invention, the extracting conveyor includes a device for applying to a workpiece a mark indicating at least in part the detached internal state of the workpiece and a sorter operatively connected to the electrical circuit for selecting under the control of the microprocessor workpieces to be scrapped and workpieces to be subjected to further treatment. The feeder may include a centerer for grinding support-contact areas on a workpiece prior to the delivery thereof to the pressing station and an oiling apparatus for applying an oil film to a part of the external surface of a workpiece, including the ground contact areas, thereby facilitating a workpiece, including the ground contact areas, thereby facilitating a sound-transmitting coupling between the workpiece and the support.

The electrical circuit is connected to the workpiece-position monitors for detecting the completion of bending operations and, as heretofore described, for ascertaining the curvature of a workpiece prior to the commencement of straightening to determine the optimal horizontal positioning of the ram. A signal converter connected to the electrical circuit and to the feeder controls the functioning thereof at least partially in response to signals from the workpiece-position monitors.

A gag-press assembly according to my present invention enables a fine quality control, due in part to the testing of each individual workpiece both before and during straightening operations. The integration of the testing apparatus at the pressing station obviates the need for a separate testing station, thereby reducing space requirements and conveyance machinery for transferring workpieces to and from the testing site. The simultaneous execution of testing and pressing operations facilitates a quicker and more accurate localization of the causes of blank defects, in part because the contribution of the press itself to the creation or aggravation of flaws is readily detectable. Metal members straightened by a gag-press assembly according to my present invention have fewer failures upon installation than pieces straightened by conventional press assemblies.

A gag press according to my present invention provides for savings in raw materials as well as in time and energy.

It is to be noted that the initial pressure-wave pulse is produced by the press ram upon the striking thereby of the workpiece.

BRIEF DESCRIPTION OF THE DRAWING

These and other features and advantages of my present invention will now be described in detail, reference being made to the accompanying drawing in which.

SPECIFIC DESCRIPTION

Figure 1:
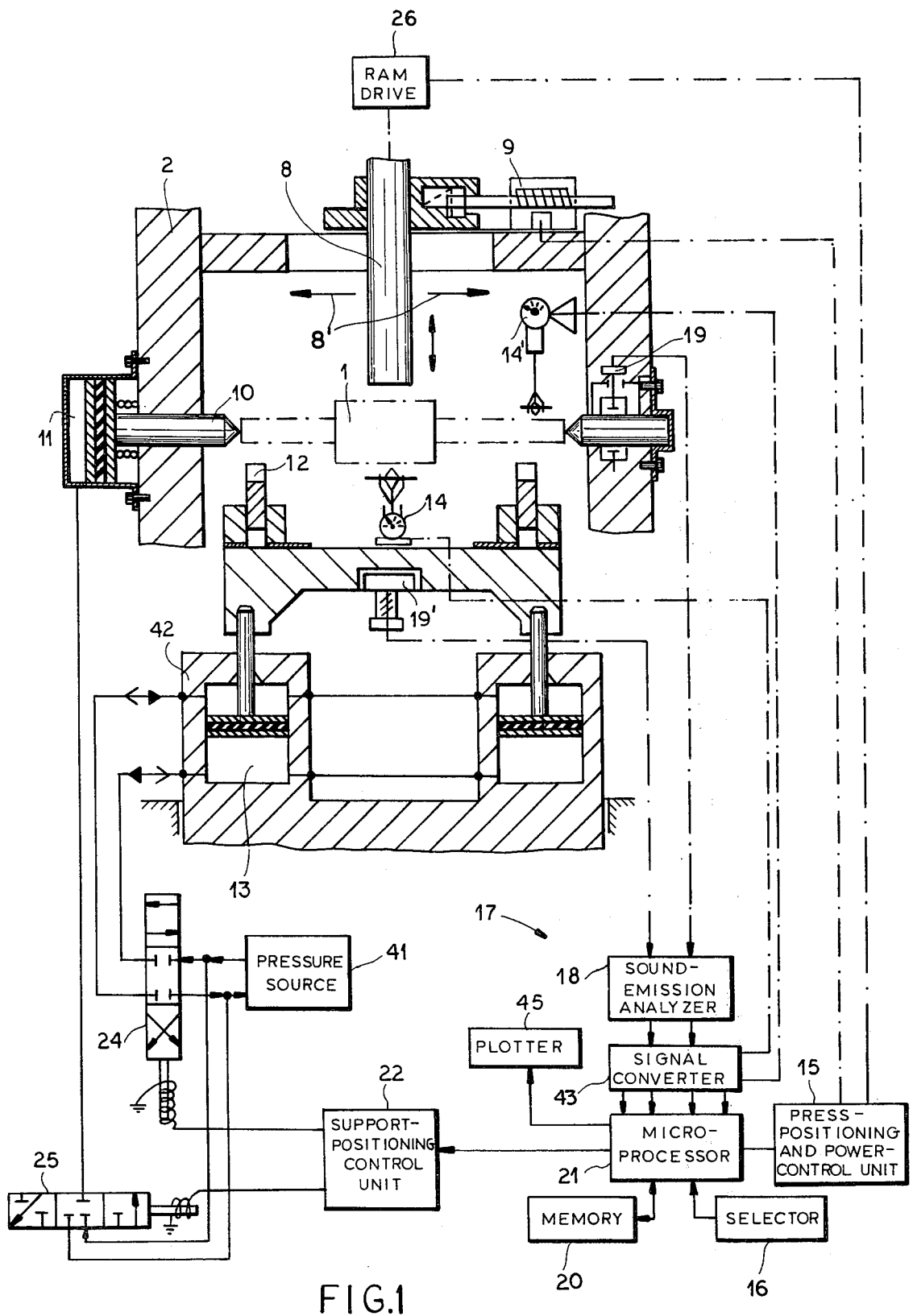
FIG. 1 is a schematic cross-sectional view of a gag press according to my present invention.
Figure 2:
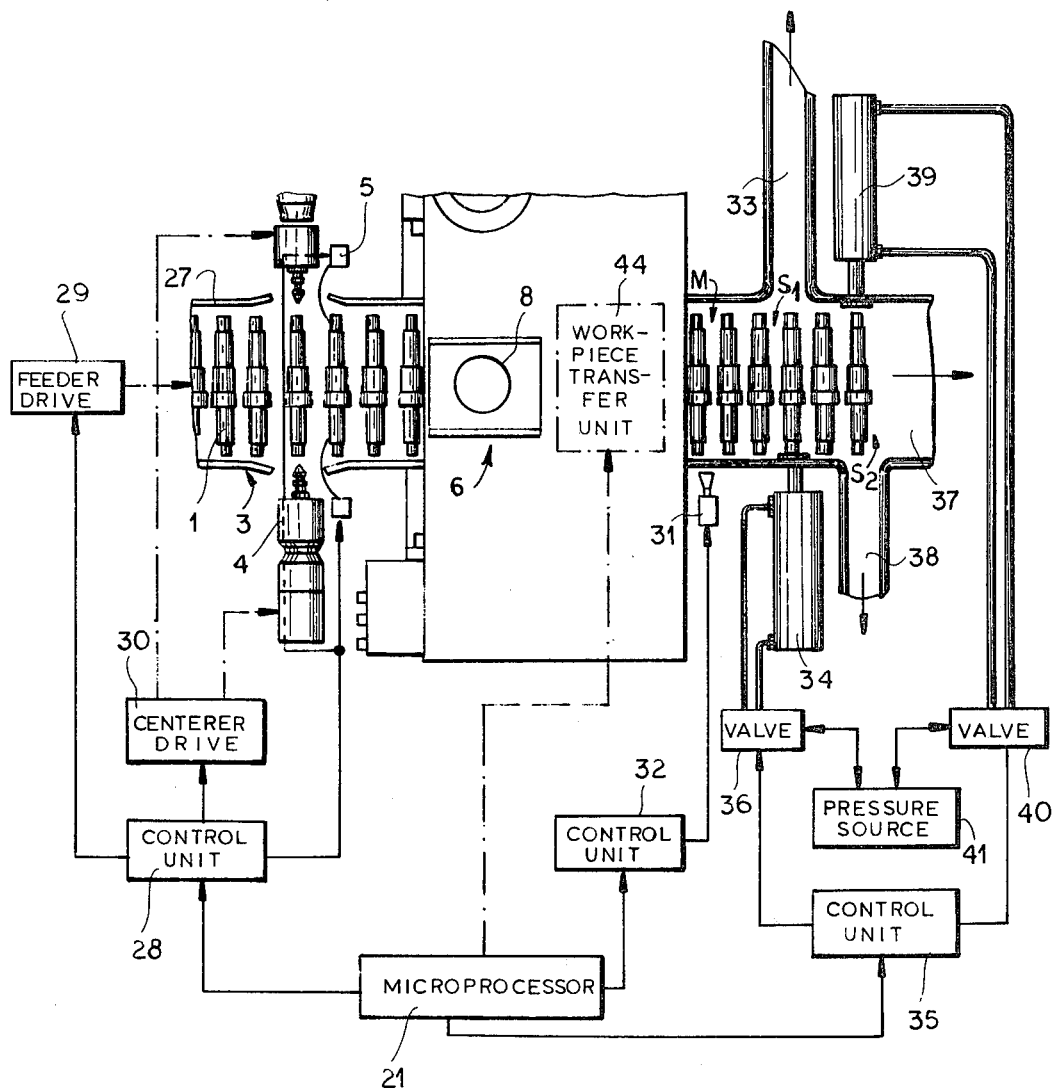
FIG. 2 is a partially schematic top view of a press assembly according to my present invention, including the press of FIG. 1 and showing a microprocessor for controlling pressing operations.

As illustrated in FIGS. 1 and 2, a gag press for straightening a blank or workpiece 1 such as a billet, bar, shaft, axle, or plate comprises a frame or superstructure 2 on which a ram 8 is mounted for vertical reciprocation by a drive 26 under the control of a microprocessor 21, as described in detail hereinafter with reference to FIG. 3. The workpiece is conveyed to a pressing station 6 by a feeding assembly 3 which may include guide walls 27 (FIG. 2) and rollers (not shown).

As illustrated in FIG. 2, a centering device 4 is juxtaposed to feeder 3 for grinding contact points or areas in the ends of the workpieces, the grinding of the contact points serving to facilitate the transmission of pressure waves from the respective workpiece over supporting members 10 or 12 to pressure-sensitive electrical transducers 19, 19'. The ground end points also facilitate the subsequent identification of the curvature of the respective workpiece by position monitors or sensors 14, 14' mounted on frame 2 and possibly including dial gauges.

A pair of oil ejectors 5 are provided downstream of the grinding device 4 for applying a film of oil to the ground contact points to further facilitate the transmission of pressure or sound waves from the respective workpieces to the support members 10 or 12. Oil ejectors 5 are controlled by microprocessor 21 via a unit 28 which serves to convert digital signals received from the microprocessor into actuating signals having a voltage and duration sufficient to energize oil ejectors 5. Control or interface unit 28 also works into a pair of drive mechanisms 29 and 30 for operating the same to actuate feeder 3 and grinder 4, respectively.

Downstream of the pressing or straightening station 6 is a marking station M at which a spot of paint is applied to each workpiece by a sprayer 31 in response to signals transmitted from a control unit 32 similar in design and function to unit 30. The paint marks are of different colors to indicate the statuses of the respective workpieces, the color applied to a workpiece being decided by microprocessor 21 at least partially in accordance with signals emitted by pressure-wave detectors or acoustic-electric transducers 19, 19', as described more fully hereinafter.

A pair of sorting stations $S_1, S_2$ are located downstream of marking station M. Station $S_1$ is defined by a first exit ramp or conveyor 33 and a first hydraulic cylinder 34 actuatable by microprocessor 21 via a control interface 35 and an electromagnetic valve 36 to transfer selected workpieces 1 from a conveyor 37 to exit ramp 33 for subsequent disposal as scrap. Station $S_2$ is analogously defined by a second exit ramp or conveyor 38 extending from conveyor 37 and a second hydraulic cylinder 39 operatively connected to microprocessor 21 via control interface 35 and another valve 40. Cylinder 39 is chargeable by valve 40 to push selected blanks from conveyor 37 to ramp 38 for feedback to a heat-treatment or tempering station (not shown) upstream of feeder 3. Valves 36 and 40 are connected to a source 41 of fluidic pressure, such as a pump.

As illustrated in FIG. 1, ram 8 is movably mounted on frame 2 (arrows 8') for positional adjustment in a horizontal plane, whereby the vertical line of action of the ram may be varied by microprocessor 21 in accordance with curvature data from position monitors 14 and 14'. The horizontal position of ram 8 is adjusted by a hydraulic, mechanical or electromagnetic device 9 in response to signals transmitted from a press-positioning and power interface unit 15 under the control of microprocessor 21, this interface unit also being connected to ram drive 26 for selectively modifying the velocity and power of a downward stroke of the ram and for interrupting a downward ram stroke upon the emission of an interrupt command by microprocessor 21.

Workpiece support members 12 are mounted on a carriage or platen 42 whose vertical position is adjustable through the action of hydraulic cylinders 13 connectable to pressure source 41 via an electromagnetic valve 24 energizable by a control unit 22 in response to digital signals emitted thereto by microprocessor 21. The horizontal positions of supports 12 may be adjusted in an analogous manner by additional hydraulic cylinders (not shown).

One or both support members 10 may form the plunger of a spring-loaded hydraulic cylinder 11 which may be charged by pressure source 41 upon the energization of an electromagnetic valve 25 by control unit 22 in response to signals from microprocessor 21.

Microprocessor 21 forms part of an electronic or electrical circuit 17 having inputs extending from position monitors 14, 14' and acoustic-electric transducers 19, 19' and outputs working into valves 24, 25, positioning device 9 and ram drive 26. A sound-emissions analyzer 18 included in electronic circuit 17 receives the output signals of transducers 19, 19' and operates on these signals to separate or filter out noise from pressure- or sound-wave packets arising as reflections of an initial ram-produced pulse from structural irregularities such as shear planes inside a workpiece. Analyzer 18 is connected at its outputs to microprocessor 21 via a signal converter 43, e.g. of the analog-to-digital type, this converter also receiving input signals from workpiece-position monitors 14, 14' for transmission to the microprocessor.

A memory 20, preferably of the programmable read-only type, is connected to the microprocessor for supplying the same with predetermined data relating to sound thresholds for respective workpiece shapes and materials. Upon comparing converted pressure-wave signals from sensors or transducers 19, 19' with threshold data from memory 20, microprocessor 21 decides whether a currently worked blank 1 is fatally defective, whether the blank has an incipiently fatal flaw which may possibly be corrected by further heat-treating, or whether the blank is acceptable for finishing operations and subsequent utilization for its intended purpose. Memory 20 may also store information pertaining to tolerance standards, the microprocessor comparing converted signals from position monitors 14, 14' with this information to determine whether a workpiece has been sufficiently bent or straightened by ram 8 in coaction with support members 10 or 12.

A selector 16 is connected to the microprocessor 21 for implementing the manual selection of data in memory 20 conforming to a series of workpieces to be processed by a gag press according to my present invention. A plotter 45 is tied to an output of the microprocessor for continuously recording the outputs of sensors 14, 14', 19, 19'.

Upon start-up of the gag-press assembly shown in FIGS. 1 and 2, microprocessor 21 emits a series of signals to control interface 28 for periodically energizing drive 29 to actuate feeder 3 for a predetermined number of intervals of essentially the same duration, thereby advancing this number of workpieces past grinding or centering station 4 and oil ejectors 5 toward pressing station 6. Further signals transmitted to interface or signal converter 28 from microprocessor 21 induce the actuation of grinder 4 and oiler 5 by unit 28. Upon the arrival of a first workpiece at pressing station 6, a transfer mechanism 44 mounted on frame 2 is controlled by microprocessor 21 to grip the first workpiece and transfer it to support members 10 or 12 (or, possibly, both), hydraulic cylinders 13 having been previously operated by unit 22 to shift platen 42 into a position coded by data stored in memory 20. In the case of support by members 10, cylinder 11 is charged to extend its respective plunger, thereby clamping the workpiece between the support members 10. Upon the transfer of the workpiece to the pressing station, microprocessor 21 emits a signal to control or interface unit 15, inducing the same to shift ram 8 into a horizontal position selected in accordance with the curvature of the workpiece as determined by microprocessor 21 from signals emitted by position sensors 14, 14' and with reference to data in memory 20.

Upon the termination of an initialization sequence 101 (see FIG. 3) with the energization of drive 26 by unit 15 in response to instructions from microprocessor 21, the same begins in a step 101 to monitor signals emitted by transducers 19 and 19', these signals being first analyzed by unit 18 and converted by unit 43. Upon comparing in a step 102 the signals from the sound sensors with threshold data from memory 20, microprocessor 21 undertakes two inquiries 103 and 104 to determine whether the analyzed and converted output signals of the sensors 19, 19' indicate the presence of a fatal defect or the presence of a flaw which may be corrected by additional heat treatment. If the microprocessor decides at inquiries 103 and 104 that the current sensor-emitted signals do not indicate any internal structural irregularities in the workpiece at the pressing station 6, the microprocessor checks at 105 the signals from the position monitors 14, 14' and compares these signals at 106 to workpiece dimension data stored in memory 20, this dimension data being selected by the microprocessor in accordance with instructions fed thereto by unit 16 under manual control. If comparison 106 shows that the currently worked blank has not yet been straightened, as ascertained by decision unit 21 in an inquiry 107, the microprocessor returns to monitoring step 101 and pressing operations continue.

Upon obtaining an affirmative reply to inquiry 103, 104 or 107, the central control unit or microprocessor terminates in a step 108, 109 or 110 the straightening operations of the press assembly by emitting signals to interface unit 15 for inducing the same to lift the ram into its retracted position and by energizing transfer unit 44 to remove the workpiece from supports 10 or 12 and to deliver it to conveyor 37. The microprocessor then memorizes at 111, 112 or 113 the status of the removed workpiece as "scrap", "reheat" or "accept", respectively.

Upon the termination of straightening operations, whether due to the detection of a flaw or to the successful completion of straightening, microprocessor 21 enters a first sequence of steps 114–117 in which interface unit 28 is induced to actuate drive 29 to energize feeder 3 for a pre-established time interval to advance a next workpiece 1 to pressing station 6, another workpiece 1 to the grinding or centering device 4 and yet another workpiece to the oiling apparatus 5. Upon the completion of the feeder advance, as ascertained by microprocessor 21 at decision junction 116, the grinding device and the oiling apparatus are actuated by unit 28 in response to signals from the microprocessor (step 117).

In a subsequent sequence of steps 118–120, the status of a workpiece disposed at station M is marked on the workpiece by sprayer 31 under the control of microprocessor 21 and interface 32 and the status of a blank at sorting station $S_1$ is checked. If at a decision junction 121, the blank at sorting station $S_1$ is discovered to be "scrap", central control unit 21 emits a signal in a step 122 to interface 35 for causing the actuation of cylinder 34. The extension of the plunger of cylinder 34 pushes the blank from station $S_1$ onto exit ramp 33 for delivery to a scrap pile. Microprocessor 21 then implements a check 123 of the status of the blank located at sorting station $S_2$; if this status is found at a decision junction 124 to be "reheat", interface unit 35 is controlled by microprocessor 21 to actuate cylinder 39 (step 125), thereby transferring the blank from primary exit conveyor 37 to secondary exit conveyor 38 for delivery to a heat treatment plant for retempering.

Upon the actuation or nonactuation of cylinders 34 and 39 in accordance with the memorized statuses of the blanks at stations $S_1$ and $S_2$, interface 22 is activated by central control unit 21 in a step 126 to reposition platen 42 for the next workpiece to be straightened at pressing station 6. If this workpiece is not the first in a series, repositioning of the support platen will generally not be required.

Figure 3:
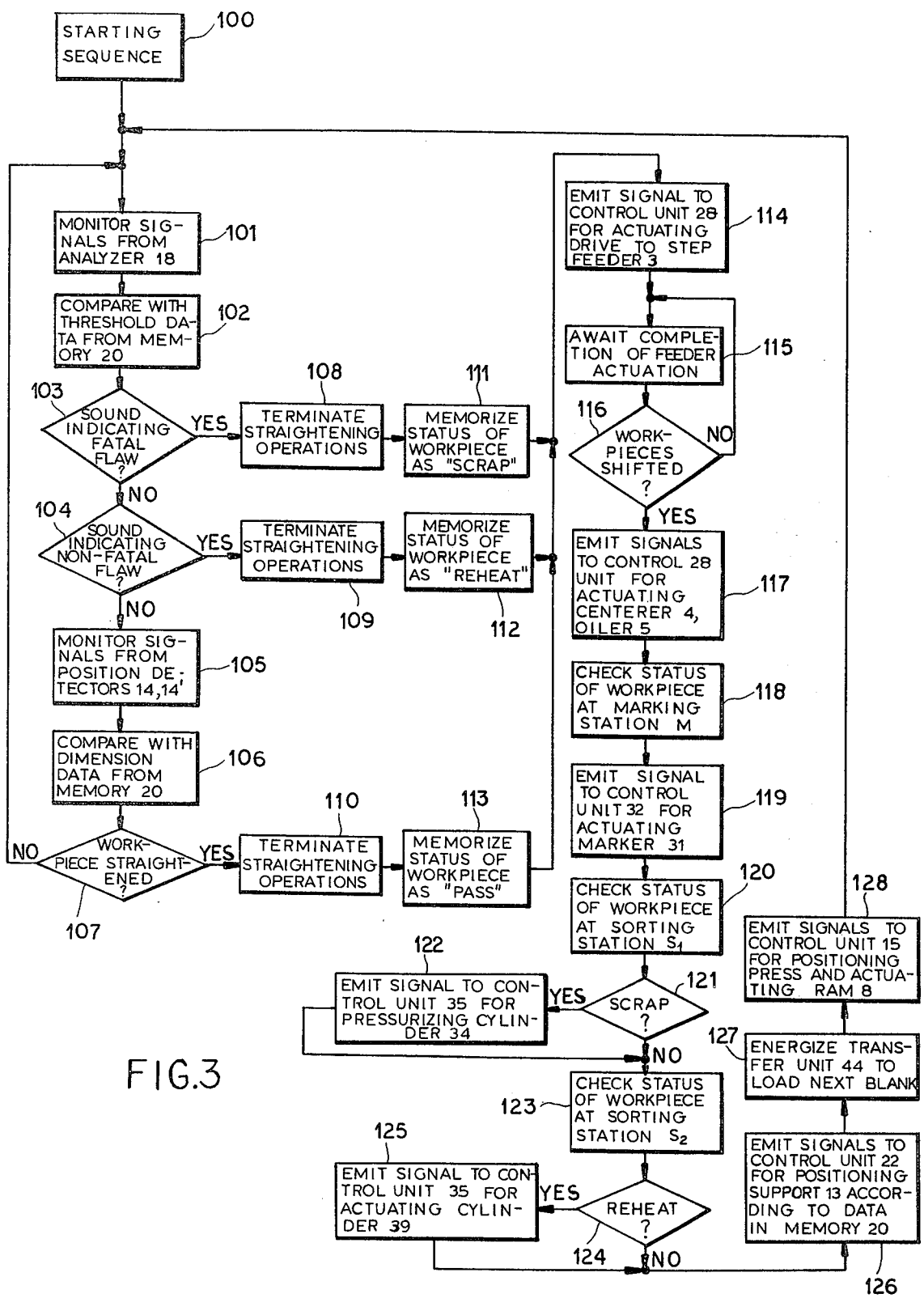
FIG. 3 is a flow-chart diagram illustrating an operational cycle of the microprocessor of FIG. 2.

As indicated in FIG. 3 at 127 and 128, an ensuing press cycle is initiated with the actuation of transfer unit 44 to load the next blank at the pressing station 6 and with the positioning and driving of ram 8 at least partially in accordance with curvature-indicating signals received by electronic circuit 17 from position monitors 14, 14′.

It is to be noted that other means may be devised, without departing from the scope of the invention, for implementing the functions of sorting assemblies 33, 34 and 38, 39 and of electronic circuit 17. Oiling apparatus 5 may, for example, be provided with a sensor for detecting the arrival of a workpiece, the oil ejectors being energized by the sensor rather than by microprocessor 21.

It is preferable that pressure-wave sensors 19 and 19′ take the form of piezoelectric-crystal transducers. In addition to a plurality of such transducers contacting the support members 10 and 12, further acoustic-electric transducers may be provided which engage ram 8 for picking up pressure waves, including ultrasonic waves, transmitted from a workpiece over the ram.

The disposition of the piezoelectric pressure-wave pick-ups at the pressing station 6 eliminates the need for a testing station inserted between the press assembly 2, 8, 9, 10, 11, 12, 13 and the marking and sorting stations M and $S_1$, $S_2$, thereby saving space, and increases the accuracy of the testing operations by omitting the placement of sensors on each workpiece to be tested. The simultaneous execution of straightening and testing operations at a single station reduces processing time, while enabling ultrasonic-wave examination of each workpiece.

I claim:

1. In a gag press for straightening a metal workpiece, comprising:

a frame;

support means on said frame at a pressing station for holding said workpiece during straightening operations in a position wherein the workpiece is straightened;

feed means extending to said pressing station for conveying said workpiece to said support means prior to said straightening operations;

stressing means including a ram reciprocatably mounted on said frame at said pressing station for striking said workpiece to generate an initial sound-producing pulse and for subsequently coacting with said support means to bend said workpiece;

drive means on said frame connected to said stressing means for reciprocating said ram in said mounting means;

extracting means for removing said workpiece from said pressing station upon the termination of said straightening operations, the improvement which comprises the combination therewith of:

sensor means including an acoustic-electric transducer mounted on said frame for detecting pressure waves including ultrasonic waves generated by internal structural irregularities in said workpiece in response to said pulse;

adjustable mounting means on said frame for holding said ram in a preselected one of a plurality of positions; and electrical circuit means connected to said sensor means for analyzing signals therefrom to determine the presence, location and extent of internal structural irregularities in said workpiece.

2. The improvement defined in claim 1 wherein said transducer contacts said support means.

3. The improvement defined in claim 2 wherein said sensor means includes an additional acoustic-electric transducer contacting said ram.

4. The improvement defined in claim 2 wherein said transducer is of the piezoelectric-crystal type.

5. The improvement defined in claim 2 wherein said electrical circuit means is operatively connected to said drive means for controlling the actuation and disengagement of said ram at least partially in response to signal from said sensor means.

6. The improvement defined in claim 5 wherein said sensor means further includes at least two workpiece-position monitors, said electrical circuit means being operatively connected to said mounting means for adjusting the position of said ram relative to said workpiece at least partially in response to signals from said workpiece-position monitors.

7. The improvement defined in claim 5 or 6 wherein said electrical circuit means includes a memory for storing coded sound-threshold values pre-established for said workpiece and control means connected to said memory and to said sensor means for comparing signals from said sensor means with said threshold values, thereby determining the presence, location and extent of internal structural irregularities in said workpiece.

8. The improvement defined in claim 7 wherein said extracting means includes sorting means operatively connected to said electrical circuit means for selecting under the control thereof workpieces to be scrapped and workpieces to be subjected to further treatment.

9. The improvement defined in claim 8, wherein said extracting means includes means for applying to a workpiece a mark indicating at least in part the internal structural state of such workpiece.

10. The improvement defined in claim 9 wherein said feed means includes means for applying an oil film to at least part of the external surface of a workpiece prior to the delivery thereof to said support means, thereby facilitating a sound-transmitting coupling between such workpiece and said support means.

11. The improvement defined in claim 10 wherein said electrical circuit means is operatively connected to said workpiece-position monitors at least in part for detecting the completion of bending operations on a workpiece, further comprising signal-converting means operatively connected to said electrical circuit means and to said feed means for controlling the functioning thereof at least partially in response to signals from said workpiece-position monitors.

12. The improvement defined in claim 11 wherein said feed means includes centering means for grinding support-contact areas on a workpiece prior to the delivery thereof to said pressing station.

* * * * *